(12) United States Patent
Rasche (10) Patent No.: US 8,108,029 B2
(45) Date of Patent: Jan. 31, 2012

(54) CATHETER NAVIGATION SYSTEM

(75) Inventor: Volker Rasche, Erbach (DE)

(73) Assignee: Koninklijke Philips Electronics NV, Eindhoven (NL)

( * ) Notice: Subject to any disclaimer, the term of this patent is extended or adjusted under 35 U.S.C. 154(b) by 852 days.

(21) Appl. No.: 11/997,421

(22) PCT Filed: Jul. 12, 2006

(86) PCT No.: PCT/IB2006/052379
§ 371 (c)(1),
(2), (4) Date: Jan. 31, 2008

(87) PCT Pub. No.: WO2007/017771
PCT Pub. Date: Feb. 15, 2007

(65) Prior Publication Data
US 2008/0221435 A1  Sep. 11, 2008

Related U.S. Application Data

(60) Provisional application No. 60/706,120, filed on Aug. 5, 2005.

(51) Int. Cl.
*A61B 5/05* (2006.01)
(52) U.S. Cl. ..................................................... 600/424
(58) Field of Classification Search .................. 600/407, 600/411, 417, 424–429, 439; 607/122–123; 128/899
See application file for complete search history.

(56) References Cited

U.S. PATENT DOCUMENTS

| | | | |
|---|---|---|---|
| 5,265,610 A | 11/1993 | Darrow et al. | |
| 5,558,091 A | 9/1996 | Acker et al. | |
| 5,568,809 A * | 10/1996 | Ben-haim | 600/433 |
| 5,671,739 A | 9/1997 | Darrow et al. | |
| 6,470,207 B1 * | 10/2002 | Simon et al. | 600/426 |
| 6,941,166 B2 * | 9/2005 | MacAdam et al. | 600/521 |
| 6,950,689 B1 * | 9/2005 | Willis et al. | 600/407 |
| 7,343,195 B2 * | 3/2008 | Strommer et al. | 600/424 |
| 7,398,116 B2 * | 7/2008 | Edwards | 600/424 |
| 7,713,210 B2 * | 5/2010 | Byrd et al. | 600/459 |
| 2001/0031919 A1 | 10/2001 | Strommer et al. | |
| 2003/0093067 A1 * | 5/2003 | Panescu | 606/32 |
| 2004/0097805 A1 * | 5/2004 | Verard et al. | 600/428 |
| 2004/0122311 A1 | 6/2004 | Cosman | |
| 2009/0182224 A1 * | 7/2009 | Shmarak et al. | 600/424 |

FOREIGN PATENT DOCUMENTS

| WO | WO9943253 | 9/1999 |
|---|---|---|
| WO | WO2004060157 | 7/2004 |

* cited by examiner

Primary Examiner — Francis Jaworski (57) ABSTRACT

A method and system for navigation of a medical instrument, including: introducing at least three reference device(s) disposed to at least three reference locations; employing an imaging and guidance system to acquire a plurality of image projections corresponding to a desired anatomy including the reference devices, the plurality of image projections being sufficient to permit generating a three-dimensional modeling or reconstruction images corresponding to the reference devices. The method also includes measuring a position of the reference devices; formulating a transformation matrix based on comparing positions of the reference devices computed from the modeling or reconstruction images with the measured positions of the reference devices; and superimposing an image of a medical instrument in at least one of the plurality of image projections based on the transformation matrix and a position of the medical instrument.

25 Claims, 4 Drawing Sheets

CATHETER NAVIGATION SYSTEM

CROSS REFERENCE TO RELATED APPLICATIONS

This application claims the benefit of International Application Number PCT/IB2006/052379, filed Jul. 12, 2006, and U.S. Provisional Application Ser. No. 60/706,120 filed Aug. 5, 2005 which are incorporated herein in whole by reference.

The present disclosure is directed to a methodology and system for a lab-only interventional three dimensional catheter navigation without pre-intervention imaging.

Intravascular interventions are conventionally carried out in a catheter laboratory. Here, the operation field is observed fluoroscopically using an X-ray system. In coronary vessel disorders, a contrasting agent is conventionally applied locally in order to show the vessel profile on the X-ray fluoroscopic image. In the course of current therapeutic methods, such as a PTCA (Percutaneous Transluminal Coronary Angioplasty) for example, a catheter is pushed into the target area, for example a stenosis in the heart of the patient, and its position is in turn monitored using X-ray fluoroscopy. This means that X-ray fluoroscopy is used not only to show the anatomy of the patient but also to navigate the catheter to its target area. Therefore, the patient and the staff require additional doses of X-radiation which serve solely for navigation.

To improve the accuracy of interventional procedures, a three-dimensional catheter localization registered to the underlying anatomy is highly appreciated especially for intracardiac procedures. Commercially available three-dimensional localization systems are expensive, often require dedicated catheters, and provide catheter localization information only. To be effective, anatomic information has to be added and registration between the anatomic coordinates and catheter coordinates is required. Currently, the anatomic information is normally provided during a pre-interventional CT or MRI scan, which requires additional procedures and adds cost. In addition, with a pre-interventional scan, the anatomic data may not represent accurately the anatomy of the day of intervention. Furthermore, data acquired with a different imaging modality have to be registered with respect to the actual imaging information used for guidance adding cost, time and complexity.

Unfortunately, these limitations currently restrict the application of 3D navigation/localization technology to more complex ablation procedures such as pulmonary vein isolation (PVI) or ventricular tachycardia (VT). To improve the current accuracy, efficiency and efficacy of less complex procedure such as the ablation of supraventricular tachycardia (SVT) and bi-ventricular pacemaker (BiV) implantation, a low-cost interventional-lab-only solution is required.

Patent Cooperation Treaty Application Publication WO 2004/060157 describes a method and an arrangement for the intravascular or intracardial navigation of a catheter. Using an X-ray fluoroscopy device, firstly an image database of 2D images is generated, where at the same time as each 2D image (I) is taken the associated heartbeat phase is recorded using an ECG. During the catheter intervention, the position of the catheter is measured by means of a position measurement unit, and at the same time, the ECG and preferably also a signal that is dependent on the breathing movement are recorded. The current spatial position of the catheter that is measured is then assigned the 2D image of the image database which corresponds in terms of the heartbeat phase and also possibly in terms of the breathing phase, on which image the position of the catheter can be represented. While this approach only utilizes 2D information for the guidance, it still requires means for doing the registration between the 2D-X-ray projection space and the localization system space.

Therefore, an interventional-lab-only approach for 3D navigation without the need for expensive pre-interventional imaging and/or registration is needed to expand applications of interventional procedures to less complex procedures with improved accuracy, efficiency and efficacy.

Disclosed herein in one or more exemplary embodiments is a method and system that utilizes the three-dimensional (3D) positions of endocardial electrodes on reference catheters simultaneously measured in the X-Ray coordinate system and a catheter localization coordinate system, for registration between the X-Ray and the catheter localization system. The 3D positions will be used for the registration, the distortion compensation, and as reference points for the 3D navigation.

According to exemplary implementations of the present disclosure, disclosed herein is a method for navigation of a medical instrument. The method includes: introducing at least three reference device(s) disposed to at least three reference locations; employing an imaging and guidance system to conduct said introducing and acquire a plurality of image projections corresponding to a desired anatomy including the at least three reference devices, the plurality of image projections being sufficient to permit generating a three-dimensional modeling or reconstruction images corresponding to the at least three reference devices. The method also includes measuring a three-dimensional position of the at least three reference devices disposed to the at least three reference locations with a position measurement system; formulating a transformation matrix based on comparing three dimensional positions of the at least three reference devices computed from the modeling or reconstruction images with the three-dimensional position of the at least three reference devices from the position measurement system; and superimposing an image of a medical instrument in at least one of the plurality of image projections based on the transformation matrix and a position of the medical instrument measured with the position measurement system.

Also disclosed herein in an exemplary embodiment is a system for navigation of a medical instrument. The system includes: at least three reference devices disposed to at least three reference locations; an imaging system configured to acquire a plurality of image projections corresponding to a desired anatomy including the at least three reference devices, the plurality of image projections sufficient to permit generating a three-dimensional modeling or reconstruction images corresponding to the at least three reference devices. The system also includes a position measurement system configured to provide data indicative of a three-dimensional position of the at least three reference devices disposed to the at least three reference locations; a controller in operable communication with the imaging system and the position measurement system, the controller configured to formulate a transformation matrix based on comparing three-dimensional positions of the at least three reference devices computed from the modeling or reconstruction images with the three-dimensional position of the at least three reference devices from the position measurement system; and the controller further configured to superimpose an image of the medical instrument in at least one of the plurality of image projections based on the transformation matrix and a position of the medical instrument measured with the position measurement system.

Further disclosed herein in another exemplary embodiment is a system for navigation of a medical instrument. The system includes: means for introducing at least three reference devices disposed to at least three reference locations;

means for employing an imaging and guidance system to conduct the introducing and acquire a plurality of image projections corresponding to a desired anatomy including the at least three reference devices, the plurality of image projections sufficient to permit generating a three-dimensional modeling or reconstruction images corresponding to the at least three reference devices; and means for measuring a three-dimensional position of the at least three reference devices disposed to the at least three reference locations. The system also includes: means for formulating a transformation matrix based on comparing three-dimensional positions of the at least three reference devices computed from the modeling or reconstruction images with the three-dimensional position of the at least three reference devices from the means for measuring; and means for superimposing an image of the medical instrument in at least one of the plurality of image projections based on the transformation matrix and a position measured with the means for measuring (60).

Also disclosed herein in yet another exemplary embodiment is a storage medium encoded with a machine readable computer program code, the code including instructions for causing a computer to implement the above-mentioned method for navigation of a medical instrument.

Further, in yet another exemplary embodiment, there is disclosed herein a computer data signal, the computer data signal comprising instructions for causing a computer to implement the above-mentioned method for navigation of a medical instrument.

Additional features, functions and advantages associated with the disclosed system and methodology will be apparent from the detailed description which follows, particularly when reviewed in conjunction with the figures appended hereto.

To assist those of ordinary skill in the art in making and using the disclosed embodiments, reference is made to the appended figures, wherein like references are numbered alike.

As set forth herein, the present disclosure advantageously permits and facilitates localization of three-dimensional (3D) positions of endocardial electrodes on reference catheters simultaneously measured in the X-Ray coordinate system and a catheter localization coordinate system, for registration between the X-Ray and the catheter localization system. The 3D positions will be used for the registration, the distortion compensation and as reference points for the 3D navigation.

The present invention may be utilized for various types of applications of 3D/4D (3D with cardiac phase) imaging. A preferred embodiment of the invention, by way of illustration, is described herein as it may be applied to X-ray imaging as utilized for electro-physiology interventions. While a preferred embodiment is shown and described by illustration and reference to X-ray imaging and interventions, it will be appreciated by those skilled in the art that the invention is not limited to the X-ray imaging or interventions alone, and may be applied to imaging systems and applications.

It will further be appreciated that while particular sensors and nomenclature are enumerated to describe an exemplary embodiment, such sensors are described for illustration only and are not limiting. Numerous variations, substitutes, and equivalents will be apparent to those contemplating the disclosure herein.

In an exemplary embodiment, a method and system to facilitate registration between the X-Ray image coordinates and the catheter localization system is disclosed. In one embodiment, 3D positions of endocardial electrodes on a plurality of reference catheters are simultaneously measured in the X-Ray fluoroscopy coordinate imaging system and the catheter localization coordinate system. A transformation matrix is then computed to quantify the transformation and thereby, registration of measurements from one system to the other. Furthermore, in an exemplary embodiment, the 3D positions are also used for distortion compensation and as reference points for the 3D navigation.

Figure 1:
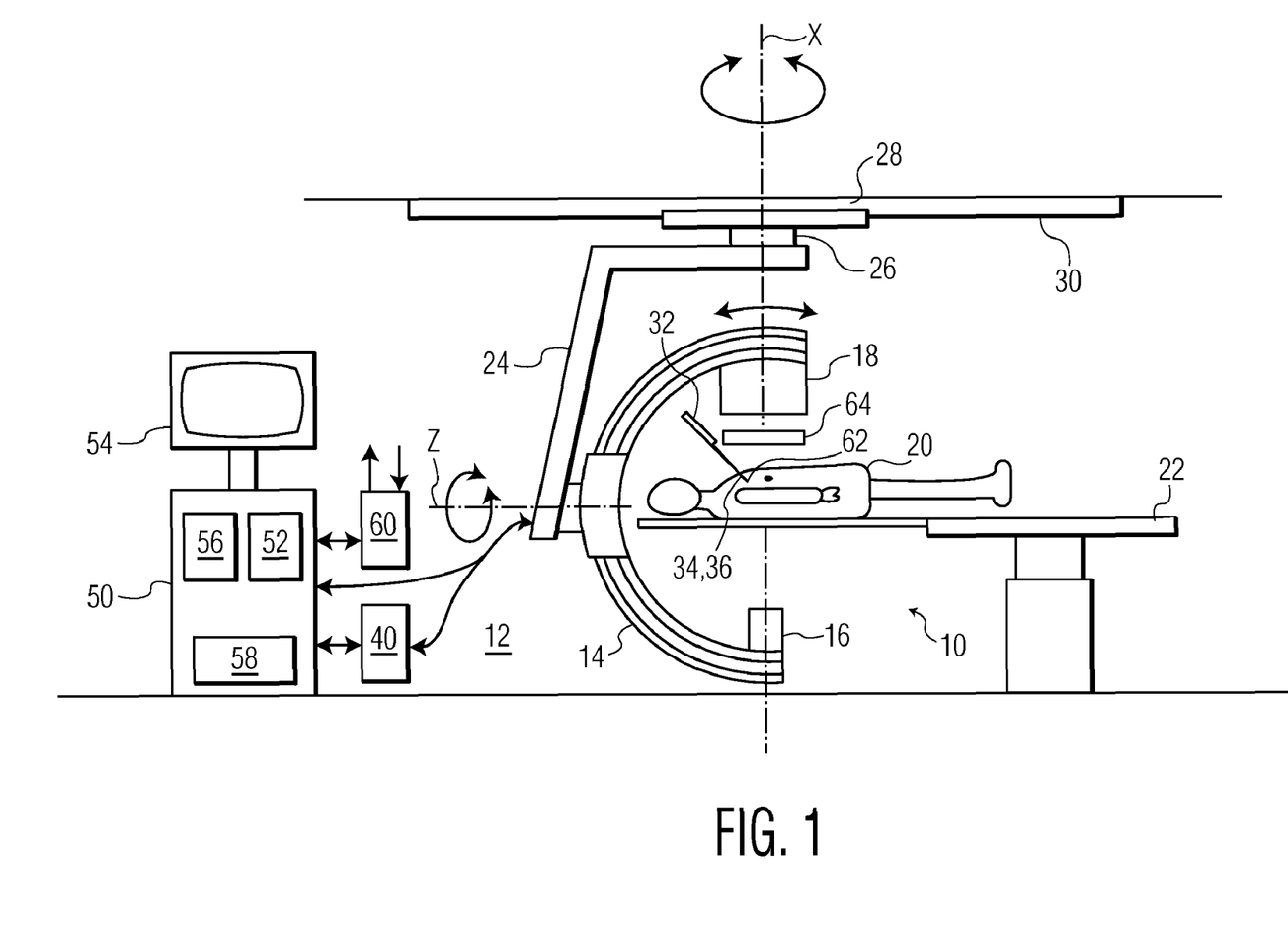
FIG. 1 depicts an X-ray imaging system in accordance with an exemplary embodiment of the invention.

Turning now to FIG. 1, a system is depicted in accordance with an exemplary embodiment of the invention. The system 10 includes an X-ray device 12 with a C-arm 14 with an X-ray tube 16 arranged at a first end and an X-ray detector 18, for example an image intensifier, arranged at its other end. Such an X-ray device 12 is suitable for forming X-ray projection images of a patient 20, arranged on a table 22, from different X-ray positions; to this end, the position of the C-arm 14 can be changed in various directions, the C-arm 14 is also constructed so as to be rotatable about three axes in space, that is, X, Z as shown and Y (not shown). The C-arm 14 may be attached to the ceiling via a supporting device 24, a pivot 26 and a slide 28 which is displaceable in the horizontal direction in a rail system 30. The control of these motions for the acquisition of projections from different X-ray positions and of the data acquisition is performed by means of a control unit 50.

Optionally, an electrocardiogram (ECG) measuring system 40 is provided with the X-ray device 12 as part of the system 10. In an exemplary embodiment the ECG measuring system 40 is interfaced with the control unit 50. Preferably, the ECG of the patient 20 is measured and recorded during the X-ray data acquisition to facilitate determination of cardiac phase. In an exemplary embodiment, cardiac phase information is employed to partition and distinguish the X-ray projection data. It will be appreciated that while an exemplary embodiment is described herein with reference to measurement of ECG to ascertain cardiac phase, other approaches are possible. For example, cardiac phase and/or projection data partitioning may be accomplished based on the X-ray data alone, other parameters, or additional sensed data.

The control unit 50 controls the X-ray device 12 and facilitates image capture and provides functions and processing to facilitate image reconstruction. The control unit 50 receives the data acquired (including, but not limited to, X-ray images, position data, and the like) so as to be processed in an arithmetic unit 52. The arithmetic unit 52 is also controlled and interfaced with the control unit 50. Various images can be displayed on a monitor 54 in order to assist the physician during the intervention.

In order to perform the prescribed functions and desired processing, as well as the computations therefor (e.g., the X-ray control, image reconstruction, and the like), the control unit 50, arithmetic unit 52, monitor 54, and reconstruction unit 56, and the like may include, but not be limited to, a processor(s), computer(s), memory, storage, register(s), timing, interrupt(s), communication interface(s), and input/output signal interfaces, and the like, as well as combinations comprising at least one of the foregoing. For example, control unit 50, arithmetic unit 52, monitor 54, and reconstruction unit 56, and the like may include signal interfaces to enable accurate sampling, conversion, acquisitions or generation of X-ray signals as needed to facilitate generation of X-ray projections and optionally reconstruction of 3D/4D images therefrom. Additional features of the control unit 50, arithmetic unit 52, monitor 54, and reconstruction unit 56, and the like, are thoroughly discussed herein.

The X-ray device 12 shown is suitable for forming a series of X-ray projection images from different X-ray positions prior to and/or in the instance on an exemplary embodiment concurrent with an intervention. From the X-ray projection images a three-dimensional image data set, three-dimensional reconstruction images, and if desired X-ray slice images therefrom may be generated. In an exemplary embodiment, the projections acquired are applied to an arithmetic unit 52, and then optionally, to a reconstruction unit 56 which forms a respective reconstruction image from the projections. The resultant 2D projections as well as 3D images can be displayed on a monitor 54. Finally, three-dimensional image data set, three-dimensional reconstruction images, X-ray projection images and the like may be saved and stored in a storage unit 58.

Continuing with FIG. 1, an exemplary embodiment of the system and methods disclosed herein facilitate using the existing X-ray imaging apparatus of a catheter laboratory, navigation of the catheter during cardiac or other intravascular interventions with a reduced amount of X-radiation dosing. Furthermore, one or more exemplary embodiments relate to an arrangement for tracking an instrument that is inserted into the body of a patient.

The system 10 also includes a position measurement unit 60 for measuring the spatial position of an instrument 32 that is inserted into the body of a patient 20 and a plurality of reference devices hereinafter referred to as probes 34. Preferably, a position measurement 60 that may be used with any off-the-shelf catheter having an electrode for a probe 34 is employed. Some of these systems employ a localization technique based on impedance measurements. Other systems employ electromagnetic sensing; however these systems, while satisfactory for catheter localization, require dedicated catheters. In such systems, the position measurement unit 60 may include, but not be limited to, a transmitter 62 for transmitting (modulated) electromagnetic fields and also a receiver 64 for receiving these fields.

The medical instrument 32 including, but not limited to, needle, catheter 36, guidewire, one or more probe(s) 34, and the like, as well as combinations including at least one of the foregoing may be introduced into the patient 20 such as during a biopsy or an intervention treatment. The position of the medical instrument 32 relative to the 2D projections and optionally three-dimensional image data set of the examination zone of the patient 20 may be acquired and measured with a position measurement system (not shown) and superimposed on the 2D projections and optionally the 3D/4D images reconstructed in accordance with an exemplary embodiment.

The system 10 includes a position measurement unit 60, such as, but not limited to, the position measurement system as described in PCT Application Publication WO 2004060157, the contents of which are incorporated by reference herein in their entirety. The position measurement unit 60 allows determination of the spatial position of the tip (e.g., probe 34) of the catheter 36, and based on the position of at least three reference probes 34, on the patient 20 in a stationary coordinate system.

Figure 2A:
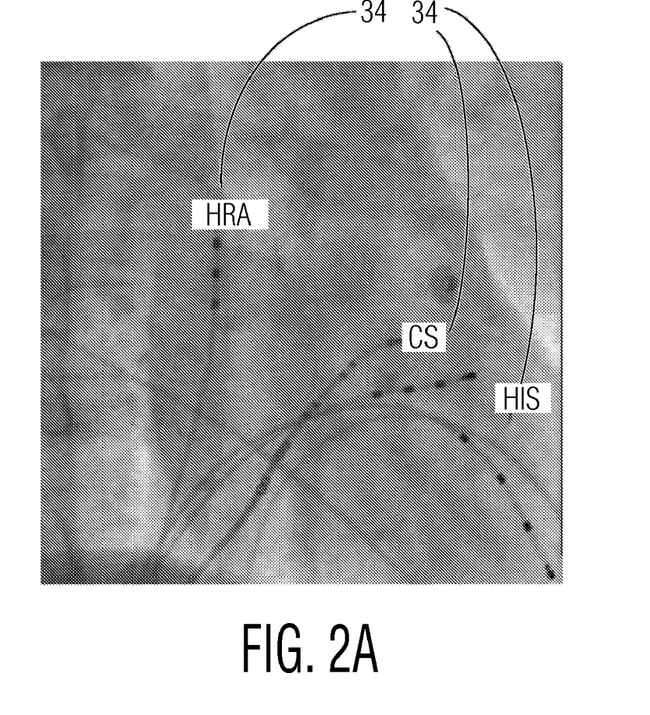
FIG. 2A depicts the placement of reference catheters at known accepted positions such as the high right atrium (HRA), the HIS bundle (HIS), and the coronary sinus (CS)
Figure 2B:
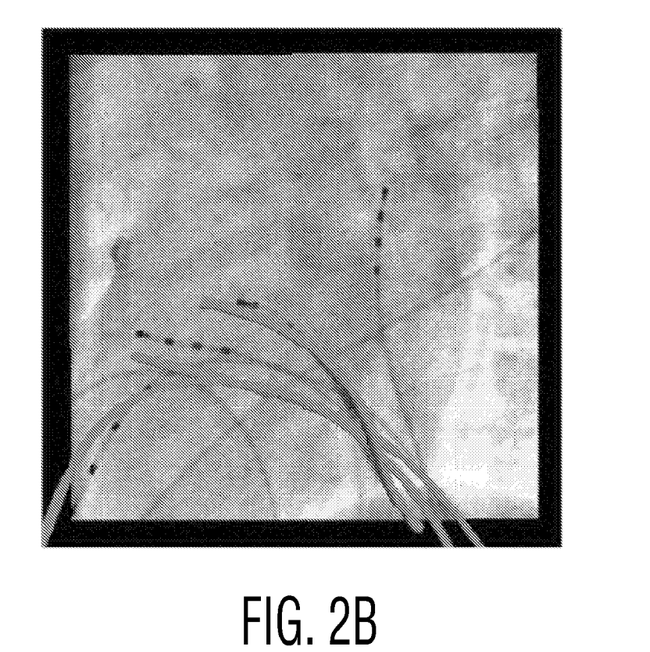
FIG. 2B depicts the reconstruction of the reference catheters from the X-ray projection data in accordance with an exemplary embodiment.

Turning now to FIGS. 2A and 2B, an exemplary embodiment of the invention will be explained by way of illustration to the field of supraventricular tachycardia (SVT) ablation procedures. In SVT procedures, three reference probes 34 are placed at known accepted positions of the high right atrium (HRA), the HIS bundle (HIS), and the coronary sinus (CS) as shown in the FIG. 2A. A methodology and system for catheter navigation according to an exemplary embodiment is implemented as follows and with reference to FIGS. 3 and 4 as well.

Figure 4:
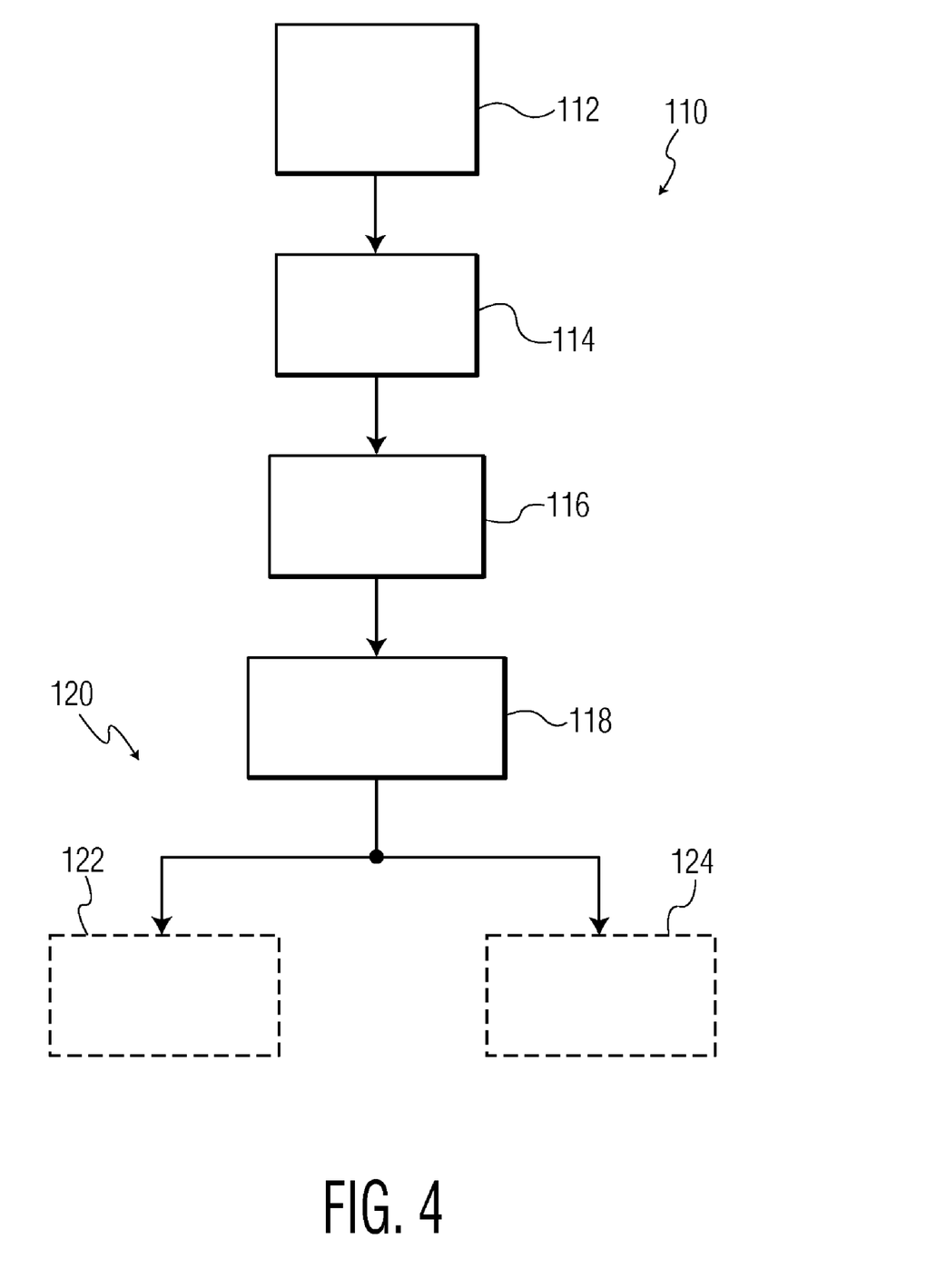
FIG. 4 depicts a flowchart in accordance with an exemplary embodiment of a methodology of catheter navigation.

FIG. 4 depicts a flowchart of a exemplary methodology 100 of catheter navigation. The process is initiated with registration shown generally as 110 between the X-Ray and catheter/device localization coordinate system followed by intervention guidance shown generally as 120 employing either navigation in 2D or navigation in 3D or both.

In an exemplary embodiment as depicted at process block 112, the registration is initiated with the introduction of a plurality of reference instruments, e.g., catheters/probes/devices and the like at selected reference positions under conventional guidance, including, but not limited to X-ray fluoroscopic guidance. As stated earlier, in one exemplary embodiment, three reference catheters 36 with probe(s) 34 at the distal ends thereof are employed and placed at the high right atrium (HRA), the HIS bundle (HIS), and the coronary sinus (CS), however other numbers and positions for the reference catheters 36 and probes 34 are possible. For example, preferably a single reference catheter 36 with at least three probes 34 is employed. At process block 114 the registration 100 continues with the acquisition of projection data, in this example, via X-ray fluoroscopy, sufficient to facilitate and enable the 3D reconstruction of the reference catheters 36 and probes 34. Simultaneously the position of the reference catheters 36 and probes 34 is measured by means of the position measurement system 60 e.g., catheter/device localization system. This projection data can be obtained either by a rotational data acquisition or by means of at least two subsequently obtained projection image series at different projection orientations. FIG. 2B depicts the reconstruction of the reference catheters from the X-ray projection data in accordance with an exemplary embodiment.

Figure 3:
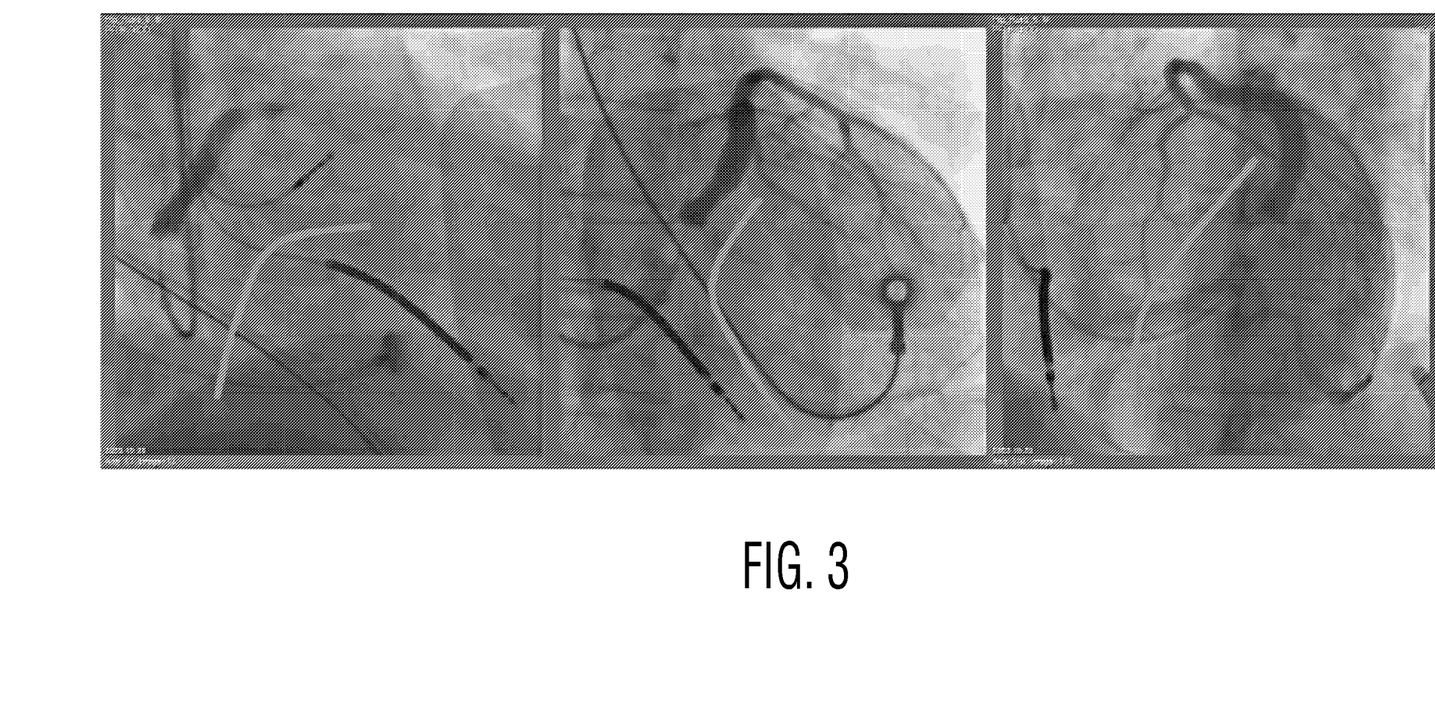
FIG. 3 depicts superimposing the measured positions of the instrument on the previously acquired projection images in accordance with an exemplary embodiment.

Continuing with FIG. 4, at process block 116, the registration 110 continues with a calculation of the 3D reference points by means of image reconstruction or modeling techniques. FIG. 3 depicts an example of this reconstruction. It should be noted that the reference catheter(s) 36 may have more than a single electrode/probe 34, so that a number of 3D points can be used if desired. A rigid or non-rigid transformation matrix is then computed between the 3D-positions as computed from the reconstructed X-ray projection data and the 3D positions as measured by the position measurement system 60 as depicted at process block 118. This transformation matrix provides the necessary conversions including, but not limited to translations, rotations, scaling, distortion corrections, and the like to transform positions measured with the position measurement system into the 2D X-ray projection data or optionally 3D reconstructed/modeled images or if desired vice versa.

Continuing with FIG. 4 and the method 100, once the registration 110 is completed and the transformation data is known, the method 100 continues with the intervention guidance 120. The intervention guidance 120 may be implemented in several different variations. In all modes, an active catheter 38 (e.g. the actual ablation catheter or pacemaker lead and the like) is tracked by the position measurement system 60 to facilitate device localization. Furthermore, in one exemplary embodiment, based on the transformation data previously discussed, the measured positions are superimposed on the previously captured 2D projection or multiple projections at different projection directions, or even all projections corresponding to the same cardiac phase out of the rotational imaging run to effect navigation in 2D as identified at process block 122. To illustrate, FIG. 3 depicts the measured positions of the instrument 32 superimposed on the previously acquired projection images. Optionally, navigation in 3D may be accomplished as depicted at process block 124 by having the measured position of the catheter/device visualized relative to the 3D reference positions. To provide anatomical information, the 3D information of the catheter/devices can be displayed fused with the projection images.

In both approaches, the visualization is preferably conducted in the same cardiac phase as the references (gated update) or being updated continuously, accepting errors in the display in phases the catheter measurements are obtained in a different cardiac phase. Advantageously, out of phase measurements are preferably indicated by some optical indicator or annunciation (e.g., a different color of the displayed catheter) and the like.

Furthermore, in another exemplary embodiment as an alternative to using a single 3D position for the reference point estimation, a 4D reconstruction (i.e., 3D at different cardiac phases) can be used as input yielding a 4D (3D plus cardiac phase) transformation between the X-ray and the catheter/device localization space.

Moreover, as an alternative to utilizing static 2D X-ray projections, projections selected out of multiple cardiac phases could be employed, thereby providing a semi-4D navigation system.

Another alternative embodiment employs continuously measured 3D location of the reference probes (34) with the position measuring system 60 and a previously computed transformation matrix generated as disclosed above for near real time calculation of another transformation of the position of the operational catheter positions to the anatomical data of the X-ray projections. This approach enables an essentially real time correction for patient motions (including respiratory motion) and even cardiac motion (different phase or changes of motion pattern due to arrhythmias) in cases where the number of reference points is sufficiently high to provide a non-rigid transformation.

In yet another alternative embodiment a 4D transformation may be employed to transform the measured catheter positions to the reference coordinate system for visualization of the movement of the catheters in a static reference. Such an approach improves accuracy, efficiency and efficacy of interventional procedures while reducing X-ray dosing during interventional procedures.

In sum, the disclosed invention advantageously permits and facilitates guidance of interventional procedures, particularly of ventricular structures and especially for less-complex ablation procedures such as the treatment of supraventricular tachycardia. Furthermore, the present disclosure permits and facilitates such guidance from a low number of projections, and results in low dose 2D interventions, interventions with 3D reconstructions or even 4D (e.g., 3D with cardiac phase). The disclosed system and methodologies provide significant benefits to operators, particularly physicians, relying on a catheter navigation system, 2D projections, or 3D/4D reconstructions for guidance and navigation during electro-physiology interventions. An additional advantage of the disclosed system and methodologies is that the registration can be performed based on a small set of X-ray projections resulting in lowered patient dosages.

The system and methodology described in the numerous embodiments hereinbefore provide a system and method which advantageously permit and facilitate guidance of interventional procedures. In addition, the disclosed invention may be embodied in the form of computer-implemented processes and apparatuses for practicing those processes. The present invention can also be embodied in the form of computer program code containing instructions embodied in tangible media 58, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

It will be appreciated that the use of "first" and "second" or other similar nomenclature for denoting similar items is not intended to specify or imply any particular order unless otherwise specifically stated. Likewise the use of "a" or "an" or other similar nomenclature is intended to mean "one or more" unless otherwise specifically stated.

While the invention has been described with reference to exemplary embodiments thereof, it will be understood by those skilled in the art that the present disclosure is not limited to such exemplary embodiments and that various changes may be made and equivalents may be substituted for elements thereof without departing from the scope of the invention. In addition, a variety of modifications, enhancements and/or variations may be made to adapt a particular situation or material to the teachings of the invention without departing from the essential spirit or scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for navigating a medical instrument, the method comprising:
introducing at least three reference devices so as to be freely disposed to at least three reference locations including high right atrium, HIS bundle, and coronary sinus;
employing an imaging and guidance system to conduct said introducing and acquire a plurality of image projections corresponding to a desired anatomy including said at least three reference devices disposed to said at least three reference locations;
generating a three-dimensional modeling or reconstruction images from the plurality of image projections, the three-dimensional modeling or reconstruction images corresponding to said at least three reference devices disposed to said at least three reference locations;

measuring a three-dimensional position for each of said at least three reference devices disposed to said at least three reference locations with a position measurement system;

formulating a first transformation matrix based on comparing three-dimensional positions of said at least three reference devices disposed to said at least three reference locations computed from said modeling or reconstruction images with said three-dimensional positions of said at least three reference devices disposed to said at least three reference locations from said position measurement system;

superimposing an image of the medical instrument in at least one of said plurality of image projections based on said transformation matrix and a position of the medical instrument measured with said position measurement system;

measuring another three-dimensional position of each of said at least three reference devices disposed to said at least three reference locations with the position measurement system;

formulating a second transformation matrix based on comparing three-dimensional positions of said at least three reference devices disposed to said at least three reference locations computed from said modeling or reconstruction images with said another three dimensional position of each of said at least three reference devices disposed to said at least three reference locations from said position measurement system; and superimposing an image of the medical instrument in at least one of said plurality of image projections based on said second transformation matrix and said position measured with said position measurement system, thereby compensating said image for motion based on said three-dimensional positions of said at least three reference devices disposed to said at least three reference locations.

2. The method of claim 1 wherein said measuring a three-dimensional position of each of said at least three reference devices disposed to said at least three reference locations with a position measurement system is conducted substantially simultaneously with said acquiring said plurality of image projections.

3. The method of claim 1 further including acquiring data indicative of motion or a phase of motion of said at least three reference devices disposed to said at least three reference locations.

4. The method of claim 3 wherein said acquiring data indicative of motion or a phase of motion is conducted substantially concurrent with said acquiring said plurality of image projections.

5. The method of claim 3 wherein said motion or phase of motion corresponds to a cardiac phase.

6. The method of claim 5 wherein said data indicative of motion or said phase of motion is an electrocardiogram.

7. The method of claim 1 wherein said formulating a transformation matrix based on comparing three-dimensional positions of said at least three reference devices disposed to said at least three reference locations is conducted for a selected cardiac phase.

8. The method of claim 1 wherein said plurality of image projections employed for said reconstruction correspond to a selected cardiac phase.

9. The method of claim 1 wherein said reconstruction is based on a subset of said plurality of image projections.

10. The method of claim 1 wherein said acquiring a plurality of image projections is conducted once.

11. The method of claim 1 further comprising:

measuring another three-dimensional position of each of said at least three reference devices disposed to said at least three reference locations with a position measurement system;

formulating a third transformation matrix based on comparing said three-dimensional positions of said at least three reference devices disposed to said at least three reference locations from said position measurement system with said another three-dimensional position of each of said at least three reference devices disposed to said at least three reference locations from said position measurement system;

superimposing an image of the medical instrument in at least one of said plurality of image projections based on said transformation matrix, said third transformation matrix, and said positions measured with said position measurement system.

12. The method of claim 1, wherein the medical instrument is a needle, a catheter, an ablation catheter, a pacemaker lead, or a guidewire.

13. The method of claim 1, wherein the medical instrument contains one or more probes that are tracked by the position measurement system.

14. The method of claim 1, wherein the three-dimensional positions of the at least three reference devices disposed to said at least three reference locations are measured continuously to provide real time correction for patient motions.

15. A system for navigating a medical instrument comprising:

at least three reference devices adapted to be freely disposed to at least three reference locations including high right atrium, HIS bundle, and coronary sinus;

an imaging system configured to acquire a plurality of image projections corresponding to a desired anatomy including said at least three reference devices disposed to said at least three reference locations, the imaging system configured to generate from said plurality of image projections a three-dimensional modeling or reconstruction images corresponding to said at least three reference devices disposed to said at least three reference locations;

a position measurement system configured to provide data indicative of a three-dimensional position of each of said at least three reference devices disposed to said at least three reference locations and the medical instrument;

a controller in operable communication with said imaging system and said position measurement system, said controller configured to formulate a transformation matrix based on comparing three-dimensional positions of said at least three reference devices disposed to said at least three reference locations computed from said modeling or reconstruction images with said three-dimensional positions of said at least three reference devices disposed to said at least three reference locations from said position measurement system; and said controller further configured to superimpose an image of the medical instrument in at least one of said plurality of image projections based on said transformation matrix and a position of the medical instrument measured with said position measurement system;

said position measurement system further configured to provide data indicative of another three-dimensional position of each of said at least three reference devices disposed to said at least three reference locations;

said controller further configured to formulate a second transformation matrix based on comparing three-dimensional positions of said at least three reference devices disposed to said at least three reference locations computed from said modeling or reconstruction images with said another three dimensional position of each of said at least three reference devices disposed to said at least three reference locations from said position measurement system; and said controller further configured to superimpose an image of the medical instrument in at least one of said plurality of image projections based on said second transformation matrix and said position measured with said position measurement system, thereby compensating said image for motion based on said three-dimensional positions of said at least three reference devices disposed to said at least three reference locations.

16. The system of claim 15 further including a system for acquiring data indicative of motion or a phase of motion of said at least three reference devices disposed to said at least three reference locations.

17. The system of claim 15 wherein said acquiring data indicative of motion or a phase of motion is conducted substantially concurrent with said acquiring said plurality of image projections.

18. The system of claim 15 wherein said motion or phase of motion corresponds to a cardiac phase.

19. The system of claim 15 wherein said data indicative of motion or said phase of motion is an electrocardiogram.

20. The system of claim 15 wherein said plurality of image projections employed for said reconstruction correspond to a selected cardiac phase.

21. The system of claim 15 wherein said acquiring a plurality of image projections is conducted once.

22. The system of claim 15 wherein said employing, measuring, formulating, and superimposing is conducted repetitively.

23. The system of claim 15 wherein said position measurement system is at least one of an impedance based system or an electromagnetic localization system.

24. A system for navigating a medical instrument comprising:

means for introducing at least three reference devices adapted to be freely disposed to at least three reference locations including high right atrium, HIS bundle, and coronary sinus;

means for imaging to acquire a plurality of image projections corresponding to a desired anatomy including said at least three reference devices disposed to said at least three reference locations, the means for imaging configured to generate from said plurality of image projections a three-dimensional modeling or reconstruction images corresponding to each of said at least three reference devices disposed to said at least three reference locations;

means for measuring a three-dimensional position of each of said at least three reference devices disposed to said at least three reference locations;

means for formulating a transformation matrix based on comparing three-dimensional positions of said at least three reference devices disposed to said at least three reference locations computed from said modeling or reconstruction images with said three-dimensional positions of said at least three reference devices disposed to said at least three reference positions from said means for measuring;

means for superimposing an image of the medical instrument in at least one of said plurality of image projections based on said transformation matrix and a position of the medical instrument measured with said means for measuring;

said means for measuring a three-dimensional position further configured to provide data indicative of another three-dimensional position of each of said at least three reference devices disposed to said at least three reference locations;

said means for formulating a transformation matrix further configured to formulate a second transformation matrix based on comparing three-dimensional positions of said at least three reference devices disposed to said at least three reference locations computed from said modeling or reconstruction images with said another three dimensional position of each of said at least three reference devices disposed to said at least three reference locations from said position measurement system; and said means for superimposing an image further configured to superimpose an image of the medical instrument in at least one of said plurality of image projections based on said second transformation matrix and said positions measured with said position measurement system, thereby compensating said image for motion based on said three-dimensional positions of said at least three reference devices disposed to said at least three reference locations.

25. A non-transitory tangible storage medium encoded with a machine readable computer program code, the code including instructions for causing a computer to implement a method for navigating a medical instrument, the method comprising:

introducing at least three reference devices so as to be freely disposed to at least three reference locations including high right atrium, HIS bundle, and coronary sinus;

employing an imaging and guidance system to conduct said introducing and acquire a plurality of image projections corresponding to a desired anatomy including each of said at least three reference devices disposed to said at least three reference locations;

generating a three-dimensional modeling or reconstruction images from the plurality of image projections, the three-dimensional modeling or reconstruction images corresponding to each of said at least three reference devices disposed to said at least three reference locations;

measuring a three-dimensional position of each of said at least three reference devices disposed to said at least three reference locations with a position measurement system;

formulating a first transformation matrix based on comparing three-dimensional positions of said at least three reference devices disposed to said at least three reference locations computed from said modeling or reconstruction images with said three-dimensional positions of at least three reference devices disposed to said at least three reference locations from said position measurement system;

superimposing an image of the medical instrument in at least one of said plurality of image projections based on said transformation matrix and a position of the medical instrument measured with said position measurement system;

measuring another three-dimensional position of each of said at least three reference devices disposed to said at least three reference locations with the position measurement system;

formulating a second transformation matrix based on comparing three-dimensional positions of said at least three reference devices disposed to said at least three reference locations computed from said modeling or reconstruction images with said another three dimensional position of each of said at least three reference devices disposed to said at least three reference locations from said position measurement system; and superimposing an image of the medical instrument in at least one of said plurality of image projections based on said second transformation matrix and said positions measured with said position measurement system, thereby compensating said image for motion based on said three-dimensional positions of said at least three reference devices disposed to said at least three reference locations.

* * * * *